United States Patent [19]
Kruse et al.

[11] 3,963,788
[45] June 15, 1976

[54] POLYHYDRIC ALCOHOL PRODUCTION USING RUTHENIUM ZEOLITE CATALYST

[76] Inventors: Walter M. Kruse, 1 Woodbury Court; Leon W. Wright, 215 Oakwood Road, both of Wilmington, Del. 19803

[22] Filed: Nov. 5, 1974

[21] Appl. No.: 520,926

Related U.S. Application Data

[63] Continuation-in-part of Ser. No. 498,969, Aug. 20, 1974, abandoned.

[52] U.S. Cl. .......................... 260/635 C; 252/455 Z
[51] Int. Cl.² .................................... C07C 31/18
[58] Field of Search ............................. 260/635 C

[56] References Cited
UNITED STATES PATENTS

| | | | |
|---|---|---|---|
| 2,868,847 | 1/1959 | Boyers | 260/635 C |
| 3,055,840 | 11/1962 | Koch | 260/635 C |

*Primary Examiner*—James O. Thomas, Jr.
*Assistant Examiner*—G. T. Breitenstein

[57] ABSTRACT

Process for the conversion of carbohydrates to polyhydric alcohols. Carbohydrates, such as corn starch hydrolyzate, glucose, and invert sugar, are converted to polyhydric alcohols by hydrogenation at high pressure in the presence of a ruthenium-containing alumino-silicate zeolite catayst in which the silica/alumina mol ratio is greater than three, and in particular ruthenium on a Y type zeolite in the hydrogen form. This acid stable catalyst gives good conversion with high selectivity to sorbitol when corn starch hydrolyzate in aqueous solution is used as the starting material.

13 Claims, No Drawings

POLYHYDRIC ALCOHOL PRODUCTION USING RUTHENIUM ZEOLITE CATALYST

RELATED APPLICATION

This application is a continuation-in-part of our co-pending application Ser. No. 498,969, filed Aug. 20, 1974 now abandoned.

BACKGROUND OF THE INVENTION

This invention relates to processes for the conversion of carbohydrates to polyhydric alcohols. More particularly, this invention relates to processes for the production of polyhydric alcohols from carbohydrates using a ruthenium metal loaded zeolite catalyst.

The term "carbohydrate" as used throughout the specification and claims includes monosaccharides and polysaccharides. This term includes both pure compounds, such as glucose and sucrose, and mixtures such as corn starch hydrolyzate, which is a hydrolysis product of corn starch containing glucose (dextrose) and oligomers thereof.

The term "polysaccharide" as used in the specification and claims includes those saccharides containing more than one monosaccharide unit. This term encompasses disaccharides and other saccharides containing a small number of monosaccharide units, which are commonly known as oligosaccharides.

The term "conversion" as used herein refers to hydrogenation when applied to monosaccharides and to a combination of hydrogenation and hydrolysis when applied to polysaccharides.

Catalytic processes may be broadly divided into processes using heterogeneous catalysts and those using homogeneous catalysts. Heterogeneous catalysts are those which are insoluble in the reaction medium, and are typically solid materials. Homogeneous catalysts are those which are soluble in the reaction medium, and are typically liquid. This invention is concerned with processes using a heterogeneous catalyst.

The conversion of carbohydrates to polyhydric alcohols using ruthenium on a solid carrier is known. U.S. Pat. No. 2,868,847 discloses the use of ruthenium on an inert catalyst support such as carbon, alumina, silica, or kieselguhr as a catalyst for the catalytic hydrogenation of saccharides such as dextrose, levulose, sucrose, maltose, and lactose. Starting materials include monosaccharides, e.g. dextrose and levulose, and disaccharides, e.g. sucrose, lactose, and maltose. Dextrose was hydrogenated to sorbitol and sucrose and lactose were hydrolyzed and hydrogenated to hexitols. However, maltose, a disaccharide containing two glucose units, was more easily converted to maltitol, a $C_{12}$ alcohol, according to the patent.

The supported nickel catalysts described in U.S. Pat. Nos. 3,538,019 and 3,670,035 (which is a division of U.S. Pat. No. 3,538,019) have high activity for the conversion of both monosaccharides and polysaccharides, including carbohydrate mixtures such as corn starch hydrolyzate, with high selectivity to sorbitol when either corn starch hydrolyzate or dextrose is used as the starting material. Carbon, diatomaceous earth, and kieselguhr are disclosed as carriers. This represents a significant improvement over the process and catalyst of U.S. Pat. No. 2,868,847, since the relatively inexpensive corn starch hydrolyzate, or other commercially available carbohydrate mixtures, can be used as the starting material in place of the much more expensive pure sugars. A disadvantage of the catalyst in U.S. Pat. Nos. 3,538,019 and 3,670,035 is that the catalyst cannot be regenerated; when reactivation is required, it is necessary to remove the active catalyst material from the support by chemical means and then to redeposit the catalyst metal on the support. Various other nickel catalysts for conversion of carbohydrates to polyhydric alcohols are cited in U.S. Pat. Nos. 3,538,019 and 3,670,035.

The hydrogenation of monosaccharides using a supported ruthenium, palladium, platinum, or nickel catalyst (activated carbon was used as the support in all experimental work) is discussed in an article by N. A. Vasyunina et al., "Catalytic Properties of Ruthenium in Monosaccharides Hydrogenation Reaction", in *Izvestiya Akademii Nauk SSR Khimicheskaya Seriya* 4:848–854 (1969). Ruthenium was found to have higher activity than the other three catalysts.

A two stage process for hydrogenation of ligneous and other plant material such as wood sawdust is disclosed in *Izv. Akad Nauk SSR, Otd. Khim.* 8: 1522–1523 (1960). The process consists of a first stage hydrolytic hydrogenation of polysaccharides in an acid medium, followed by a second stage hydrogenation of the lignin in an alkaline medium, using a ruthenium catalyst in both stages. In a specific embodiment, pine sawdust is treated using an aqueous phosphoric acid medium and a ruthenium on carbon catalyst. The first stage reaction product is filtered to separate the liquid medium from the crystals obtained from the first stage filtrate.

The use of solid ruthenium-containing zeolite catalysts for hydrogenation reactions other than the hydrogenation of carbohydrates is also known. U.S. Pat. Nos. 3,200,082 and 3,200,083 disclose catalysts comprising noble metals including ruthenium on zeolites X, Y, and L. U.S. Pat. No. 3,767,720 discloses the hydrogenation of aromatic hydrocarbons (e.g., benzene) to cyloolefins using various catalysts including ruthenium on 3A, 4A, 10X, and 13X molecular sieves. Other references disclosing ruthenium-containing zeolite catalysts include U.S. Pat. Nos. 3,197,398; 3,239,451; 3,269,934; 3,324,047; 3,364,135; 3,375,205; 3,459,676; 3,476,821; 3,524,809; 3,600,301; and 3,647,681.

Zeolites A and X are essentially crystalline synthetic aluminosilicate zeolites having a silica/alumina mol ratio less than 3. Zeolite A is described and claimed in U.S. Pat. No. 2,882,243 and zeolite X is described and claimed in U.S. Pat. No. 3,882,244, both issued to Union Carbide Corporation. Zeolites Y and L are essentially crystalline synthetic aluminosilicates having silica/alumina mol ratios greater than 3, i.e., from 3 to about 6 in zeolite Y, and from about 5.2 to about 6.9 in zeolite L.

Zeolite Y (sodium form) is described in U.S. Pat. No. 3,130,007, and decationized zeolite Y is disclosed in U.S. Pat. No. 3,130,006, also both issued to Union Carbide Corporation. Zeolite L. is described and claimed in U.S. Pat. No. 3,216,789, also issued to Union Carbide. Some more recent references, such as U.S. Pat. No. 3,324,047 and G. T. Kerr, "Molecular Sieves", Advances in Chemistry Series No. 121 (American Chemical Society), pages 219–228 (1973), state that "decationized zeolite Y" and "Hydrogen zeolite Y" (i.e., the hydrogen form of zeolite Y) are the same. Zeolites are ordinarily synthesized in the sodium form; other metallic or ammonium ions can be introduced into the zeolite by ion exchange, as is well known in the art. Zeolites in the hydrogen form can be obtained by decomposition of the ammonium form at high temperature, according to methods known in the art. The structure of zeolites is discussed extensively in D. L. Breck, "Zeolite Molecular Sieves", published by John Wiley and Sons, New York, 1974. A comprehensive review of zeolite catalysts is contained in an article by J. Turkevich, *Catalysis Reviews*, 1, 1–35 (1967).

Although various catalytic processes for the conversion of carbohydrates to polyhydric alcohols are known in the art, none possesses all of the attributes which are desirable in such processes, e.g., ability to use inexpensive mixed carbohydrates; high selectivity to sorbitol when either glucose or a starch hydrolyzate is used as the starting material; high catalyst attrition resistance; and ease of catalyst regeneratability.

SUMMARY AND OBJECTS

An object of this invention is to provide an improved process for the preparation of polyhydric alcohols from carbohydrates.

This and other objects will be apparent from the specification which follows.

According to the present invention, a polyhydric alcohol is produced from a carbohydrate by contacting said carbohydrate in an aqueous medium with hydrogen at elevated temperature and pressure in the presence of a catalyst comprising a ruthenium-containing aluminosilicate zeolite having a silica/alumina mol ratio of at least about 3.

DESCRIPTION OF THE PREFERRED EMBODIMENT

The process of the present invention may be broadly characterized as a process for the conversion of carbohydrates to polyhydric alcohols. The conversion of a monosaccharide is a hydrogenation process. Conversion of polysaccharides involves both hydrolysis and hydrogenation. Excellent yields of desired polyhydric alcohols, with minimal quantities of unconverted sugar and by-products, are obtained by using a ruthenium zeolite catalyst of the type that will be described below. Carbohydrate starting materials and process conditions (except for catalyst/carbohydrate ratio) specified herein are conventional; use of a particular type of ruthenium zeolite catalyst as will be described is the key to the excellent results obtained in the present process.

Catalyst

The catalysts for use in the process of this invention are crystalline or essentially crystalline aluminosilicate zeolites of the molecular sieve type having a silica/alumina mol ratio of at least 3 and containing a minor catalytically effective amount of ruthenium. The preferred zeolites are synthetic. The ruthenium content of the catalyst is in the range of about 0.1% to about 5%, preferably about 0.5% to about 3%, of the total catalyst weight. The ruthenium is present as the free metal finely dispersed on the surfaces of the zeolite, which serves both as a support and as an acid catalyst for the hydrolysis of polysaccharides.

The zeolites are crystalline aluminosilicates in which the aluminum, silicon, and oxygen atoms are arranged in a rigid three-dimensional network having internal cavities of molecular size and pores of uniform size which provide access to these cavities. The crystal network includes $SiO_4$ and $AlO_4$ tetrahedra; the electro-negativity of the latter is balanced by cation (e.g., metal ions, ammonium ions, or hydrogen ions). The crystal structure of zeolites has been discussed extensively in the literature and will not be discussed at length here.

Preferred ruthenium-containing zeolite catalysts are the ruthenium metal-loaded Y type zeolite catalysts. Y type zeolites are characterized by a silica/alumina mol ratio of at least about 3, and effective pore size of at least about 8 Angstrom units in the hydrogen form, and a three-dimensional network of channels. Examples of catalyst of this type are ruthenium on Ultrastable Faujasite Y (hydrogen form), ruthenium on zeolite Y (hydrogen form), and ruthenium on calcined zeolite SK-89. Ultrastable faujasite Y (hydrogen form) is commercially available from the Davison Chemical Division of W. R. Grace and Company and is described in U.S. Pat. No. 3,293,192 and in C. V. McDaniel and P. K. Maher, Society of Chemical Industry (London) Monograph No. 186 (1968); P. K. Maher, F. D. Hunter, and J. Scherzer, "Molecular Sieves", Advances in Chemistry Series No. 101 (American Chemical Society), pages 266–276 (1971); J. Scherzer and J. L. Bass, *Journal of Catalysis*, 28, pp. 101–115 (1973). According to U.S. Pat. No. 3,293,192, the "ultrastable" zeolite described therein has a silica/alumina mol ratio of about 3.5 to 7, and an alkali metal content less than 1%. This zeolite is prepared in the hydrogen form, but can be converted to other cationic forms; among the cations mentioned in the patent are platinum "and other Group VIII" metal ions (no Group VIII metals other than platinum are specifically named). Zeolite Y (hydrogen or "decationized" form) is commercially available from Linde Division of Union Carbide Corporation, New York, N.Y., and is described in U.S. Pat. No. 3,130,006 cited supra. Both ultrastable faujasite Y (hydrogen form) and zeolite Y (hydrogen form) can be synthesized from the sodium form of zeolite Y. Ultrastable faujasite Y is a material of improved thermal stability in which a portion of the aluminum originally present in the zeolite crystal structure has been removed. Another highly desirable Y type zeolite catalyst is ruthenium on calcined zeolite SK-89. Zeolite SK-89 is available from Linde Division of Union Carbide Corporation.

The ruthenium-containing zeolite catalysts of this invention may be prepared from the corresponding zeolites in the hydrogen form by ion exchange with an aqueous solution of a simple ruthenium salt, e.g. ruthenium trichloride, followed by reduction of ruthenium to the metallic state. A simple ruthenium salt, rather than a complex salt (e.g., a ruthenium ammine salt), should be used. Ion exchange may be accomplished by known techniques, e.g. suspending particles of the zeolite (hydrogen form) in an aqueous slurry with stirring for a time sufficient to effect ion exchange, and then separating the ruthenium/zeolite particles from solution by conventional means such as filtration and drying the ruthenium/zeolite particles. This gives the unreduced form of the catalyst, in which ruthenium is present as a cation in the trivalent state. Usually the catalyst is utilized in the reduced form. The reduced form may be prepared by reducing the ruthenium cation to the metallic state with hydrogen in the dry state at a temperature of about 100° to about 300°C. and preferably from about 100° to 200°C. The activity of the catalyst is dependent on the reduction temperature; optimum activity is obtained when the reduction temperature is about 120° to about 160°C. At temperatures about 160°C. the catalytic activity gradually diminishes as the reduction temperature rises. Alternatively, trivalent ruthenium can be reduced in situ in the reaction medium, simultaneously with the catalytic conversion of carbohydrate, during the first cycle of operation. Reduction in situ eliminates the separate reduction step, which is required in preparing nickel catalysts, and thus gives a simpler and more economical catalyst preparation process.

The presence of large quantities of sodium in the catalyst is detrimental to catalytic activity when the starting carbohydrate is a polysaccharide-containing material such as corn starch hydrolyzate. The alkali metal content in that case is preferably not more than about 1% of total catalyst weight. The presence of ammonia (in the form of ammonium ions) in the catalyst likewise appears to be deleterious. Catalysts having an alkali metal content in excess of about 1% exert a buffering action on the reaction medium, and make it difficult or impossible to maintain the pH of the reaction medium sufficiently low to achieve complete hydrolysis of the polysaccharides present. The alkali metal and ammonia contents of the zeolite prior to impregnation with ruthenium determine the final alkali metal and ammonia contents of the catalyst; therefore zeolites having a low alkali metal and ammonia contents should be used in preparing catalysts to be used with polysaccharide-containing carbohydrates. The alkali metal content of the catalyst is not important when the starting carbohydrate is a monosaccharide (e.g., glucose) or a mixture of monosaccharides.

The presence of metal ions other than alkali metal ions in a catalyst is not harmful, provided the catalyst contains sufficient hydrogen ions to give the reaction medium the required acidity for hydrolysis of polysaccharides when the starting carbohydrate is a polysaccharide-containing material. For example, ruthenium on zeolite catalysts which contain either alkaline earth metal ions (e.g., magnesium) or rare earth ions (e.g., cerium) are known in the art and may be used in the present process.

The ruthenium-containing Y type zeolite catalysts are especially advantageous as compared to prior art catalysts when the starting material is corn starch hydrolyzate or other starch or cellulose hydrolyzate. These catalysts give sorbitol of high purity with minimal quantities of isomers (e.g., mannitol and iditol) and other impurities and with minimal quantities of unconverted sugar in the product. These catalysts, in common with zeolite catalysts generally, have good attrition resistance which is more than sufficient for use in a liquid phase system and which exceeds the attrition resistance of catalysts having carbon carriers such as ruthenium on carbon. The ruthenium-containing Y type catalysts are readily regenerated by a simple acid wash. Ruthenium on ultrastable faujasite Y has greater acid stability than ruthenium on zeolite Y, so that smaller catalyst losses occur on regeneration. Ruthenium on zeolite SK-89 gives shorter reaction times than other ruthenium-containing Y type zeolite catalysts, which permits greater product output per unit of equipment.

Ruthenium on synthetic mordenite (hydrogen form) catalysts, which are characterized by pores of about 5–7 angstrom units in diameter and a two-dimensional channel structure, can also be used as catalysts according to the present invention, although they are less desirable than ruthenium on a Y zeolite. The preparation of these catalysts is analogous to the preparation of the ruthenium on Y type zeolite catalysts, described above. Although the ruthenium/mordenite catalysts possess high activity, they are not readily regenerated by acid washing as are the ruthenium/zeolite Y catalysts.

Ruthenium on zeolite X catalysts have been found to give very poor activity as catalysts for the hydrogenation of carbohydrates. This reflects the poor hydrolytic stability of zeolite X relative to zeolite Y or mordenite, as is known in the art.

Amorphous supports, such as amorphous silica, alumina, or silica-alumina, are not suitable in the present process. A ruthenium on amorphous silica-alumina catalyst was found to give excessive quantities of by-products when used for the catalytic conversion of corn starch hydrolyzate to sorbitol. By way of contrast, nickel on zeolite Y has been found to be unsatisfactory as a carbohydrate conversion catalyst, while certain nickel catalysts on amorphous silica carriers have been previously found quite suitable for this purpose (see U.S. Pat. Nos. 3,538,019 and 3,670,035 cited supra).

A composite catalyst comprising a ruthenium metal-loaded zeolite as described above, such as ruthenium on a Y type zeolite, and a binder or matrix material, such as clay or amorphous silica-alumina, may be used as the catalyst if desired.

STARTING MATERIAL

Both monosaccharides and polysaccharides can be converted into polyhydric alcohols according to the present invention. Therefore, the carbohydrate starting material can be a monosaccharide or mixture thereof, or a polysaccharide-containing material. The latter term encompasses disaccharides and mixtures thereof, as well as carbohydrates comprising both a monosaccharide (or monosaccharides) and a polysaccharide or polysaccharides. The starting materials for the present process are known in the art as starting materials for the production of polyhydric alcohols by catalytic hydrogenation in the case of monosaccharides, or hydrolysis and hydrogenation in the case of polysaccharides.

Monosaccharides which may be hydrogenated to polyhydric alcohols according to this invention contain at least 4 (usually 4 to 7) carbon atoms; the pentoses and hexoses are the most important members of the class. Both aldoses (i.e., compounds having a terminal aldehyde or —CHO group) and ketoses (i.e., compounds having a keto or >CO group) can be treated. Illustrative examples of monosaccharides which may be converted to polyhydric alcohols in accordance with the process of this invention include glucose, fructose, galactose, mannose, arabinose, ribose and xylose. Mixtures of monosaccharides, and in particular invert sugar (a mixture of glucose and fructose) can also be treated according to this invention; however, mixtures ordinarily should be simple mixtures that give simple mixtures of polyhydric alcohols that are easily separated.

Disaccharides which can be converted into polyhydric alcohols according to the present process include sucrose, maltose, lactose, cellobiose, and melibiose. Raffinose is a suitable trisaccharide starting material.

Other polysaccharide-containing starting materials include starch and starch decomposition products such as dextrin, glucose syrups, cellulose hydrolyzates, and starch hydrolyzates, e.g., corn starch hydrolyzate. Preferred polysaccharide-containing starting materials are those in which all of the polysaccharide units are polymers of glucose. The starch hydrolyzates, such as corn starch hydrolyzate are examples of such polymers. Other polysaccharide-containing carbohydrates in which all polysaccharide units are polymers of the same monosaccharide, such as inulins (which are polyfructosides) and vegetable ivory (a polymannoside), can also be used.

Corn starch hydrolyzate is a particularly preferred starting material in the present process because of its low cost. Other starch hydrolyzates are similar in composition to corn starch hydrolyzate and can also be used with good results. Corn starch hydrolyzate is a by-product of the hydrolysis of corn starch to glucose. The hydrolyzate as produced contains some impurities, including electrolytes, which are detrimental in the present process; these impurities can be removed by treatment with a combination of a cation exchange resin and an anion exchange resin. The cation exchange resin can be either a strongly acid or weakly acid resin in the hydrogen form. The anion exchange resin is a weakly basic resin in the hydroxyl form; a strongly basic resin should not be used since this causes isomerization of some of the glucose present. The purified corn starch hydrolyzate, which is used as a starting material for the present process, consists essentially of glucose (D-glucose or dextrose) and polymers thereof (primarily low molecular weight polymers or oligosaccharides, e.g., di-, tri-, and tetrasaccharides) which are composed entirely of glucose units and which therefore yield glucose as the only monosaccharide on hydrolysis. An outstanding feature of the present invention is that inexpensive and readily available carbohydrates such as corn starch hydrolyzate can be used as starting materials with good yields of the desired polyhydric alcohol or alcohols (sorbitol when a starch hydrolyzate is the starting material) and with minimal quantities of by-products and sugars in the reaction product.

Preferred polysaccharide starting materials are those which are readily hydrolyzable to monosaccharides, that is, which can be hydrolyzed to monosaccharides under dilute acid conditions such as those used in the process of this invention. High molecular weight polysaccharides, such as cellulose and insoluble starch (e.g., corn starch) can be used but generally require more severe conditions of hydrolysis than those contemplated in the present invention. These materials are more advantageously partially hydrolyzed according to the methods known in the art with the formation of a hydrolyzate such as starch or cellulose hydrolyzate. Wood sawdust is unsuitable as a starting material because it contains a mixture of polysaccharides and lignin, which is acid-insoluble.

Monosaccharides containing an aldehyde group (i.e., aldoses) are hydrogenated almost exclusively by the process of this invention to a polyhydric alcohol containing the same number of carbon atoms, and with a hydroxyl group attached to the aldehyde carbon atom in place of the oxygen atom. Glucose, for example, is hydrogenated almost exclusively to sorbitol. (The presence of isomers such as mannitol and iditol is probably due to isomerization of sobitol). Monosaccharides containing a keto group in the molecule (i.e., ketoses) are hydrogenated to a mixture of approximately equal amounts of two different polyhydric alcohols. Both resulting polyhydric alcohols contain the same number of carbon atoms as the monosaccharide with the same space configuration of units attached to the carbon atoms, but one of the polyhydric alcohols has a hydroxyl grop on one side of the keto carbon atom in place of the oxygen atom, and the other polyhydric alcohol has the hydroxyl group on the opposite side of the keto carbon atom in place of the oxygen. Fructose, for example, has a keto group at the second carbon atom and the molecule is hydrogenated to approximately equal amounts of sorbitol and mannitol. Invert sugar, which consists of equimolar quantities of glucose and fructose, is hydrogenated to a reaction product containing approximately 3 mols of sorbitol for each mol of mannitol.

Polysaccharides are hydrolyzed to their basic monosaccharide (or monosaccharides) whose aldehyde or ketone groups are then hydrogenated to hydroxyl groups to produce the desired polyhydric alcohol (or alcohols) of the monosaccharide. Those polysaccharides having free aldehyde or ketone groups in their molecular structure before they are subjected to the process of this invention may have these groups hydrogenated at the same time the molecule is hydrolyzed. At any rate, both hydrolysis and hydrogenation reactions appear to take place simultaneously when polysaccharides are subjected to the process of the invention and the reaction results in the desired polyhydric alcohol (or alcohols) of the basic structural monosaccharides. Polysaccharides composed of different monosaccharide units are hydrolyzed and hydrogenated to the polyhydric alcohols of the respective monosaccharides. When sucrose (whose basic structural monosaccharides are glucose and fructose) is hydrolyzed, and hydrogenated, the resulting reaction product is a sorbitol-mannitol mixture in the molar ratio of approximately 3/1. Corn starch hydrolyzate (in which the polysaccharides consist of glucose units) yields sorbitol, with isomers thereof (e.g., mannitol and iditol) present only in small by-product amounts.

PROCESS

The present process uses an aqueous reaction medium. The carbohydrate or carbohydrates to be subjected to the process of this invention are dissolved in water at the appropriate concentration for the conversion reaction. Concentrations of carbohydrates from about 20% to about 80% by weight are usually employed for the reaction. Carbohydrate concentrations in the range of about 40% to about 70% by weight react particularly smoothly in the reaction and such concentrations are, therefore, the more preferred for this invention. It is not necessary for the carbohydrates to form true solutions with the water, as suspensions and colloidal solutions of carbohydrates readily react.

The amount of catalyst to be used in the process of this invention may vary over a wide range and will depend upon the particular catalyst, carbohydrate, temperature, and pressure which are employed in the process. Polysaccharides tend to require a high level of catalyst than the monosaccharides. In general, catalyst concentrations required when using the catalysts herein tend to be appreciably lower than those used for nickel catalysts. Catalyst concentrations ranging from about 0.01% to about 0.1%, preferably from about 0.02% to about 0.05% by weight of total ruthenium based on the weight of carbohydrate are suitable.

The reaction can be carried out either in one stage or two stages. More than two stages can be utilized but this is seldom necessary or advantageous. Excellent results can be obtained with one stage when a monosaccharide or mixture of monosaccharides is treated. However, two stage operation is preferred when a polysaccharide-containing carbohydrate, such as corn starch hydrolyzate, is used as the starting material, because two stage operation results in better conversions to the desired polyhydric alcohol or alcohols with smaller amounts of impurities. The second stage in a two stage operation is generally conducted at a higher temperature than the first stage. Reaction pressures are typically about the same in both stages. The advantage of two stage treatment is that more effective hydrolysis of polysaccharides is achieved in this manner. When a starting material containing both a monosaccharide and polysaccharide (e.g., corn starch hydrolyzate) is used, it appreears that hydrogenation of the monosaccharide content occurs in the first stage, while hydrolysis of the polysaccharides and hydrogenation of the monosaccharides thus produced occurs primarily in the second stage.

The pressures and temperature employed in the process of this invention may vary over wide limits. The reaction may be carried out at temperatures from about 100°C. to about 200°C. and at hydrogen pressures of at least about 100 psig. The preferred ranges of pressure and temperature are from about 1000 psig to about 3000 psig and from about 140°C. to about 180°C. respectively. Generally, lower temperatres are preferred for the hydrogenation of monosaccharides than for the conversion of polysaccharide-containing starting materials. Monosaccharides are advantageously hydrogenated at about 100° to about 160°C. Polysaccharide-containing starting materials, on the other hand, require a temperature of at least about 170°C. during at least a portion of the reaction period. When a polysaccharide-containing carbohydrate such as corn starch hydrolyzate is treated in a two stage process according to this invention, the preferred first stage temperatures are in the range of about 100° to about 175°C., preferably about 120° to about 160°C., and second stage temperatures range from about 170°C. to about 200°C., preferably about 175° to about 180°C. It is to be understood that higher and lower pressures and temperatures than those described above may be used when deemed necessary or desirable.

The time of reaction will depend upon the specific carbohydrate or carbohydrates being acted upon, the specific hydrogenation catalyst used, pressure, temperature, and the concentration of the carbohydrate. Generally, the time may be about 30 to 180 minutes. However, some reactions may take longer or shorter periods of time; in any event, the reaction should be continued until the hydrolysis and hydrogenation have been completed.

Longer reaction times are usually required for the treatment of polysaccharide-containing starting materials than for the hydrogenation of monosaccharides. The hydrogenation of a monosaccharide or monosaccharides is ordinarily complete in an hour or less, while the total reaction time in a two stage treatment of a polysaccharide-containing carbohydrate is typically about 1 to 3 hours, with the first stage lasting about 0.5 to 1.5 hours and the second stage requiring about 0.5 hour to about 2 hours.

Reaction times substantially longer than those required should be avoided whenever a reaction temperature above about 160°C. is used. The catalysts used herein catalyze the isomerization of sorbitol at temperatures above 160°C., so that mannitol and in some cases iditol will be produced if contact between the catalyst and the reaction medium is continued for an unnecessarily long time.

The pH of the reaction medium is at least about 3 and preferably at least about 3.5. At pH values below about 3.0, and to a lesser extent at values below about 3.5, the zeolite catalyst tends to lose part of its crystallinity with consequent deterioration due to acid attack. The rate of deterioration increases as the pH is decreased. Also, it appears that the formation of certain by-products, notably hexitans such as 1,4-sorbitan, is increased as the pH value falls below about 3. It is to be understood that higher and lower pressures and temperature than those described above may be used when deemed necessary or desirable.

When the starting material is a polysaccharide-containing material such as corn starch hydrolyzate or other starch hydrolyzate, the pH of the reaction medium should be in the range of about 3.0 to about 4.5, preferably from about 3.5 to about 4.0. It appears more important to maintain the pH range during the latter portion of the reaction (e.g., during the second stage) than during the first portion. At reaction product pH values about 4.5 and to a lesser extent at values about 4.0, hydrolysis of polysaccharides is incomplete and sugars are present in the reaction product. The use of a catalyst containing no more than about 1% alkali metal by weight is important in achieving the desired pH. An acid can be added to the reaction medium, either at the outset or during the reaction, e.g., between the first and second stages (the latter is ordinarily preferred) for pH control. Common mineral acids, such as sulfuric acid and phosphoric acid give good results. Hydrochloric acid can also be used but is harmful to stainless steel equipment.

Monosaccharides such as glucose can be hydrogenated over a much wider pH range than polysaccharide-containing carbohydrates. Both acidic and neutral media (e.g., media having a pH to about 7.5) are suitable for hydrogenation of monosaccharides. Catalysts in which the zeolite support is in the sodium form can be used when the starting material is a monosaccharide.

The reactants may be added to the reaction chamber in any suitable manner or in any suitable order. It is preferred to add the catalyst to the aqueous solution or suspension of the carbohydrate and then add the hydrogen under pressure and commence heating the mixture to the desired temperature.

The reaction is carried out in any suitable type of apparatus which enable intimate contact of the reactants and control of the operating conditions and which is resistant to the high pressures involved. The process may be carried out in batch, semi-continuous, or continuous operation. Batch operation in a conventional autoclave gives excellent results.

Upon completion of the reaction, the catalyst is removed by filtration or decantation and the polyhydric alcohol may be separated from the filtrate by any suitable means, such as filtration, washing, crystallization, solvent extraction, or evaporation. Any electrolytes which may be present in the filtrate may be removed prior to recovery of the polyhydric alcohols by passage through a mixed ion exchange bed which contains both a cation exchange resin and an anion exchange resin.

The catalyst is readily regenerated by washing with a dilute aqueous mineral acid, such as sulfuric acid, hydrochloric acid, or phosphoric acid at room temperature. Acid concentrations ranging from about 0.01 N to about 0.5 N can be used. While acid concentrations higher than 0.5 N effectively regenerate the catalyst, they also cause partial loss of crystallinity of the zeolite (due to dissolution of part of the alumina) and therefore should be avoided. The acid wash is preferably followed with a water wash. When the catalyst is separated from the reaction product by filtration, the wet catalyst may be acid washed on the filter. The catalyst should be acid washed after each use when a starch or cellulose hydrolyzate is treated; failure to acid wash usually results in appreciably reduced activity during the next use. Less frequent regeneration will suffice when the starting material is a monosaccharide. A complete operating cycle includes reaction of a carbohydrate as above described followed by catalyst regeneration. This regeneration method can also be applied to other supported ruthenium catalysts, e.g., ruthenium on carbon, which have been used for the conversion of carbohydrates to polyhydric alcohols. Higher acid concentrations can be used in regenerating a ruthenium on carbon catalyst than are permissible in regenerating a ruthenium on zeolite catalyst.

A major advantage of the catalysts used in the present invention is that they can be regenerated by a simple acid wash, and do not require removal from the carrier (i.e. by dissolution) or redeposition on the carrier.

Another major advantage of the catalysts used herein is that they give good yields of desired polyhydric alcohols with minimal quantities of undesired polyhydric alcohols, other impurities, and unconverted sugars in the reaction product, even when inexpensive and readily available polysaccharide-containing carbohydrates such as corn starch hydrolyzate are used.

Another important advantage of ruthenium on zeolite catalysts over ruthenium catalysts on other supports, such as carbon, is that the ruthenium zeolite catalysts are physically more rugged. This is particularly important in continuous and semi-continuous operations, where attrition can occur.

EXAMPLES

This invention will now be described further with respect to the examples which follow. All percentages refer to percentage by weight unless otherwise indicated. Product analyses are on the dry basis unless otherwise reported. The term "corn starch hydrolyzate," wherever used in the examples, refers to a corn starch hydrolysis product containing on the dry basis, 63% (by weight) glucose, about 17% disaccharides, about 4% trisaccharide about 3% tetrasaccharides, and about 12% higher polysaccharides, which has been treated with an anion exchange resin and a cation exchange resin in order to remove impurities.

EXAMPLE 1

CATALYST PREPARATION

A solution of ruthenium trichloride was prepared by dissolving 0.5 grams of $RuCl_3$ (40% Ru; Engelhard) in 200 ml. of distilled water. To this solution in a 1-liter beaker was added a slurry of 20 grams of Ultrastable Faujasite Y ($H^+$ form: 0.5% Na) (W. R. Grace & Company, Davison Chemical Division) in 300 ml. of distilled water. The slurry was heated on an electric hotplate with magnetic stirring at 70°–80°C. for 1 hour. The slurry was filtered and washed with 350-ml. portions of distilled water. The colorless filtrate was shown to contain less than one part per million of ruthenium. The ruthenium-exchanged Ultrastable Faujasite Y was dried for 2 hours at 140°C. in a vacuum oven. The dried product was slurried in water and reduced at 120°C. and 50 psig. for 2 hours, then dried at 140°C. The resulting catalyst contained 1% by weight of ruthenium and 0.5% by weight of sodium.

CONVERSION OF CORN STARCH HYDROLYZATE

Five successive operating cycles were carried out in which corn starch hydrolyzate was converted to sorbitol in a two stage process using the catalyst described above, followed by acid rejuvenation of the catalyst.

A slurry containing 100 grams of corn starch hydrolyzate, 3.00 grams of catalyst, and about 90–95 grams of water, was prepared by first dissolving the corn starch hydrolyzate in about 65–70 grams of water and then adding the catalyst and the remaining 25 grams of water, all under an inert atmosphere. The pH of the slurry (which will be called "initial pH") was determined and the slurry was charged to a 1-liter autoclave equipped with a stirrer while maintaining the inert atmosphere. Fresh catalyst was used in the first cycle; dried reused catalyst recovered from the previous cycle plus enough makeup catalyst to give a total catalyst weight of 3.00 grams was used in the subsequent cycles.

The autoclave was purged with nitrogen and hydrogen, pressurized with hydrogen to about 1500–1550 psig. at room temperature, heated to the first stage reaction temperature (160°C.) and pressure (about 2000 to 2050 psig.), and maintained at this temperature for 35 minutes. Some pressure drop (approximately 130–175 psig.) occurred during the first stage. Then 3 ml. of 0.36 N sulfuric acid, diluted to 15 ml., was added to the autoclave by displacement at about 1900–2000 psig. hydrogen pressure. The autoclave contents were heated to the second stage reaction temperature (175°C.) and pressure (about 2025–2145 psig) and were maintained at this temperature for 90–95 minutes. Some pressure drop (approximately 30–75 psig.) occurred during the second stage. The reaction temperature was maintained until a constant pressure was observed for about 30 minutes.

The autoclave contents wee cooled to room temperature, discharged from the autoclave, and filtered on a Buechner funnel to separate the catalyst from the reaction product. The pH of the filtrate (i.e., the reaction product) was determined; this value is reported as "final pH". The filtrate was concentrated to approximately 70% solids and analyzed. All analyses are reported on the dry basis.

The catalyst on the Buechner funnel was regenerated by washing with 50 ml. of 0.07 N sulfuric acid and then with 50 ml. of water and weighed after each cycle.

Operating conditions and product analyses (in weight per cent on the dry basis) for each cycle are given in Table I below. Complete analysis of the first cycle reaction product was not made because of the high sugar content, indicating incomplete hydrolysis and an unsatisfactory product. Lower yields of sorbitol and larger amounts of by-products are generally obtained with fresh catalysts then with previously used catalysts.

TABLE I

| Cycle | 1 | 2 | 3 | 4 | 5 |
|---|---|---|---|---|---|
| Catalyst reuse | 0 | 1 | 2 | 3 | 4 |
| Initial pH | 5.2 | 3.9 | 3.7 | 3.6 | 3.7 |
| Final pH | 4.5 | 4.0 | 3.8 | 4.0 | 3.6 |
| First Reaction Stage | | | | | |
| Pressure, psig. | 1990 | 2030 | 2030 | 2025 | 2050 |
| Temp., °C. | 160 | 160 | 160 | 160 | 160 |
| Time, min. | 35 | 35 | 35 | 35 | 45 |
| Second Reaction Stage | | | | | |
| Pressure, psig. | 2060 | 2150 | 2145 | 2035 | 2025 |
| Temp., °C. | 175 | 175 | 175 | 175 | 175 |
| Time, min. | 95 | 90 | 90 | 90 | 90 |
| Product Analysis | | | | | |
| Sorbitol | — | 94.0 | 92.4 | — | 93.8 |
| Mannitol | — | 2.04 | 2.47 | — | 2.95 |
| Hexitans | — | 1.29 | 3.15 | — | 2.11 |
| Total non-sugar Impurities | — | 4.07 | 6.08 | — | 5.76 |
| Reducing Sugar | 0.03 | 0.04 | 0.04 | — | 0.04 |
| Total Sugar | 3.94 | 0.36 | 0.18 | — | 0.15 |
| Sorbitol by difference | — | 95.6 | 93.7 | — | 94.1 |

Notes
1. Pressure for each reaction stage is initial pressure; some pressure drop occurs during each stage due to hydrogen consumption.
2. "Hexitans" includes 1,4-sorbitan and other hexitans.

EXAMPLE 2

The catalyst used in this example was 1% Ru on Ultrastable Faujasite Y (H+ form; W. R. Grace) containing 0.6% Na and prepared by ion exchanging a quantity of Ultrastable Faujasite Y (H+ form, 0.6% Na) with ruthenium chloride solution and reducing the ruthenium to the metallic state in a stream of flowing hydrogen at 150°C. and atmospheric pressure for 30 minutes. This catalyst was used in a total of 25 operating cycles (i.e., 24 reuses), using corn starch hydrolyzate as the starting material.

Three different modes of operation were used in different cycles in this example. The first mode, designated as Mode A, was similar to the reaction procedure of Example 1, i.e., two-stage operation with acid added at the beginning of the second stage, except for minor differences in reaction temperatures, times, and quantities of acid, and in the use of hydrochloric acid instead of sulfuric acid in one cycle. The second mode, designated as Mode B, was also a two-stage process, but acid (sulfuric or hydrochloric) was added to the initial slurry of catalyst and corn starch hydrolyzate. The third mode, designated as Mode C, was a one-stage process using a uniform reaction temperature (150° to 175°C.) throughout the cycle with acid added to the initial catalyst/corn starch hydrolyzate slurry. Separation of the catalyst from the reaction product, and analysis of the reaction product in all three modes were as described in Example 1. The catalyst was regenerated by washing with 50 ml. of 0.36 N sulfuric acid and then with water after each cycle. The fresh zeolite support had a crystallinity of 80%, and the catalyst after 25 cycles had a crystallinity of 75%.

Operating conditions and results for representative cycles are given in Table II below.

TABLE II

| Cycle | 9 | 17 | 24 | 25 |
|---|---|---|---|---|
| Catalyst Reuse | 8 | 16 | 23 | 24 |
| Mode | B | C | A | A |
| Initial pH | — | 3.0 | 4.1 | — |
| Final pH | 3.5 | 3.3 | 3.6 | 3.7 |
| First Stage | | | | |
| Temp., °C. | 160 | 170 | 175 | 160 |
| Time, min. | 30 | 120 | 30 | 45 |
| Acid added, meq. | 0.2 | 0.36 | — | — |
| Second Stage | | | | |
| Temp., °C. | 180 | One | 175 | 175 |
| Time, min. | 40 | Stage | 120 | 85 |
| Acid added, meq. | — | — | 0.36 | 0.36 |
| Product Analysis | | | | |
| Sorbitol | 90.0 | 90.0 | 92.0 | 91.6 |
| Mannitol | 2.38 | 3.14 | 2.47 | 2.18 |
| Hexitans | 2.57 | 1.50 | 2.05 | 1.68 |
| Total non-sugar impurities | 5.23 | 6.31 | 5.92 | 4.87 |
| Reducing sugar | 0.05 | 0.35 | 0.05 | 0.09 |
| Total sugar | 0.14 | 2.19 | 0.86 | 1.63 |
| Sorbitol by difference | 94.6 | 91.5 | 93.2 | 93.5 |

Good sorbitol yields were generally obtained in two-stage modes of operation. Results obtained in one-stage operations were generally satisfactory at reaction temperatures of 170°C., as illustrated by Cycle 17 but not satisfactory at temperatures of 150° and 160°C. However, a low sorbitol yield (78%) was obtained in another cycle that was run at 170° apparently due to too short a reaction time and too low a pH (2.6) at the start. There was virtually no loss in crystallinity of the catalyst, indicating that the acid concentrations used both in reaction and in regeneration were within acceptable limits.

EXAMPLE 3

3.00 grams of a reused 0.8% ruthenium on Ultrastable Faujasite Y catalyst prepared as described in Example 1, were added to 163.0 grams of 62% aqueous solution of corn starch hydrolyzate under an inert atmosphere. The resulting slurry, having a pH of about 4.6, was added to a 1-liter stirred stainless steel autoclave, the autoclave purged with nitrogen and hydrogen, and pressured to 1500 psig. with hydrogen. The autoclave was heated with stirring to 145°C. and held there for 1.5 hours. A pressure drop of 290 psig. occurred. The temperature was then increased to 190°C. and the pressure to 1625 psig., and the reaction was continued for an additional 30 minutes. The reaction product, which had a pH of 4.0, was then cooled and filtered. The filtrate was passed through a mixed bed of ion-exchange resin (a cation-exchange resin and an anion-exchange resin) and concentrated to 70% solids. The product contained 93.7% sorbitol, (by difference) 0.10% reducing sugar, and 0.80% total sugar, based on dry solids.

This example shows that operation without added acid is possible provided the temperature in the second stage is sufficiently high. Such mode of operation is ordinarily not preferred because of side reactions.

EXAMPLE 4

The catalyst used in this example was Ultrastable Faujasite Y (H+ form) containing 1% ruthenium in the trivalent form and 0.6% sodium, and was prepared as described in Example 1 except that the reduction of the ruthenium with hydrogen prior to the first cycle was omitted. This example describes the second cycle of operation.

A feed slurry having a pH of 3.6 was prepared by suspending 3.00 grams of catalyst in 167 grams of aqueous corn starch hydrolyzate solution containing 100 grams of solids. The reaction procedure of Example 1 was followed except that the first- and second-stage reaction times were 35 minutes and 90 minutes, respectively. The final pH was 4.2. Analysis of the product after filtration, ion exchange, and concentration to 70% solids showed 93.6% sorbitol (95.5% by difference), 2.66% mannitol, 1.70% 1,4-sorbitan, 4.54% total non-sugar impurities, 0.04% reducing sugar, and 0.15% total sugar.

This example shows that the ruthenium in the catalyst can be reduced to the metallic state in situ during the first cycle of operation, rather than in the dry state prior to the first use, if desired.

The reaction product of this example contained relatively large amounts of mannitol, but a low total sugar content. This was the result of too long exposure time.

EXAMPLE 5

81.0 grams of glucose were dissolved in 34.7 grams distilled water. 2.50 grams of a fresh 1% ruthenium on Ultrastable Faujasite Y ($H^+$ form) prepared as described in Example 2 were suspended in this sugar solution. This suspension was transferred to a 300-ml. stainless steel autoclave equipped with a magnetic drive stirrer. The autoclave was flushed with nitrogen and hydrogen, and pressurized to 1500 psig. $H_2$ pressure. The autoclave was heated to 110°C. and about 1700 pressure. Some pressure drop (to about 1500 psig.) occurred during reaction. The reaction essentially ceased after 1.0 hour as measured by the constancy of the pressure. The product was removed, filtered, concentrated and analyzed by gas-liquid chromatography for sorbitol and glucose. The product contained 93.5% sorbitol and 6.4% glucose, both on a dry solids basis. The product did not contain hexitol isomers such as mannitol and iditol. The low reaction temperature accounts for the incomplete conversion of glucose.

EXAMPLE 6

130 grams of a 50% aqueous solution of invert sugar was slurried with 2.50 grams of a fresh 1% ruthenium on Ultrastable Faujasite Y ($H^+$ form) catalyst prepared in the same manner as the catalyst in Example 2. The slurry was charged to a 300 ml. autoclave, which was flushed with nitrogen and hydrogen and then pressured to 1500 psig. hydrogen pressure. The autoclave was then heated to 100°C. After a reaction period of 2.0 hours at 100°C. followed by 0.5 hours at 150°C., the autoclave was cooled and the reaction product was removed, filtered, concentrated, and analyzed. The reaction product contained, by weight on the dry basis, 24.8% mannitol, 0.1% total sugar and only trace amounts of non-hexitol impurities.

EXAMPLE 7

The catalyst used in this example was 1% Ru on zeolite Y ($H^+$ form). Zeolite Y ($NH_4^+$ form), purchased from Linde Division of Union Carbide Corporation as SK-41, was calcined for 3 hours at 550°C. to give zeolite Y ($H^+$ form). This zeolite as received contained 23.0% $Al_2O_3$, 65.0% $SiO_2$ and 2.4% $Na_2O$ by weight on the anhydrous basis. The zeolite Y ($H^+$ form) was exchanged with aqueous $RuCl_3$ solution and dried, and the trivalent ruthenium was reduced to metallic ruthenium with hydrogen at 150°C.

An aqueous solution of corn starch hydrolyzate was catalytically treated with hydrogen in the presence of the above-described Ru on zeolite Y catalyst as described in Example 1. The catalyst was regenerated by acid washing after each cycle as described in Example 1, except that 0.05% phosphoric acid was used instead of sulfuric acid after the third cycle. A total of four cycles were run. Sorbitol assays (excluding the first cycle) ranged from 91.2% to 91.7% on the dry basis. Sugar values were quite low except in the fourth cycle. However, mannitol production in each cycle was fairly high, ranging from 2.54% to 4.18% (dry basis).

EXAMPLE 8

A catalyst consisting of 1% ruthenium on synthetic mordenite ("Zeolon 100", $H^+$ form) was prepared by ion exchange of 20 grams of "Zeolon 100" ($H^+$ form) (supplied by Norton Co.) with 500 mg of aqueous ruthenium chloride at room temperature. This catalyst was tested for glucose hydrogenation activity by hydrogenating an aqueous solution of glucose for 1 hour at 110°C. and 1700 psig. initial hydrogen pressure, following the procedure of Example 5. The product contained 97% sorbitol by GLC analysis.

The catalyst was recovered from the reaction product slurry by filtraton, acid wshed with 100 ml. of 0.36 N sulfuric acid and dried (2.7 grams). This catalyst and 0.3g of make-up catalyst ion again tested for glucose hydrogenation activity under conditions identical with those in the first cycle. However, in the second cycle of operations, the catalyst showed poor glucose hydrogenation activity; the reaction product contained 53% sorbitol, 42% glucose, and 4.4% hexitans. This suggests that synthetic mordenite would not be a good support for catalysts of this invention, since reusability is essential from the economic standpoint.

EXAMPLE 9

The catalyst used in this example was a 1% Ru on a Y type zeolite catalyst. The zeolite was obtained from Linde Division of Union Carbide Corporation as SK-89. The SK-89 zeolite was calcined for 4 hours at 600°C., yielding a Y type zeolite in the $H^+$ form. This zeolite was exchanged with aqueous $RuCl_3$ solution, dried and reduced at 150°C. in flowing hydrogen for 0.5 hour.

An aqueous solution of corn starch hydrolyzate was catalytically hydrogenated with 2 grams of the above described 1% Ru on zeolite catalyst (giving a Ru/carbohydrate ratio of 0.02%) essentially as described in Example 1, except that only two cycles (i.e., one cycle using fresh catalyst and one cycle employing a reused catalyst) were carried out. The first reaction stage initial pressure was 2050 psig. (dropping to 1910 psig.); the temperature was 160°C. and the reaction time 45 minutes. The second reaction stage initial pressure was also 2050 psig; the temperature was 175°C. and the reaction time was 45 minutes. The second cycle product analyzed, on the dry basis, 96.1% sorbitol, 1.80% hexitans, 1.70% mannitol, 0.17% reducing sugar and 0.61% total sugar. This example shows that the second stage reaction time can be decreased by a factor of two by use of this catalyst.

EXAMPLE 10

The catalyst in this example was a fresh 1% Ru on calcined zeolite SK-89 ($H^+$ form, Union Carbide), which was prepared in the same manner as the catalyst in Example 9.

An aqueous solution of corn starch hydrolyzate was catalytically treated with the above described 1% Ru on zeolite SK-89 catalyst according to the procedure of Example 1, except that a much lower pressure was used. The initial catalyst/carbohydrate slurry, which has a pH of 4.3, was pressured at room temperature with hydrogen to 250 psig. and then heated to 160°C. The first reaction-stage temperature was 160°C., the reaction pressure was 480 psig. (dropping to 250 psig.), and the reaction time was 45 minutes. Then 3 ml. of 0.36 N sulfuric acid was added by hydrogen displacement, and the reaction mixture was heated to 175 C. The second stage reaction pressure 490 psig. (dropping to 480 psig.) the temperature was 175°, and the reaction time was 45 minutes. The final pH was 4.0. The reaction product was found to contain 84.0% sorbitol, 7.21% mannitol, 0.22% reducing sugar, and 0.29% total sugar on the dry basis. The high mannitol production suggests that too long a reaction time was used.

EXAMPLE 11

This example shows the importance of low alkali metal content in catalysts used for conversion of corn starch hydrolyzate.

The catalysts used in this example contained 1% Ru and were prepared from a batch of Ultrastable Faujasite Y (W. R. Grace & Co.) which as received contained 1.3% Na and 5.2% $NH_3$.

One portion of this batch was ion exchanged with aqueous ruthenium chloride, dried, and treated with a flowing stream of hydrogen at 150°C. for 30 minutes to reduce the ruthenium. This catalyst contained 1% Ru, 1.3% Na, and 5.2% $NH_3$, and will be designated herein as Catalyst R.

A second portion of this batch was heated for 3 hours at 400°C., decreasing the $NH_3$ content to 0.2% but not affecting the sodium content. This portion was ion exchanged with aqueous ruthenium chloride, dried, and treated with hydrogen at 150°C. for 30 minutes. This catalyst is designated herein as Catalyst S.

A third portion of this batch was calcined for 13 hours at 450°C. in a furnace; the bed thickness was about 3 cm. The calcined material was ion exchanged with aqueous ammonium nitrate and calcined in a bed 3 cm. thick for 4 hours at 530°C. This gave a zeolite containing 0.33% Na and 0.17% $NH_3$. This material was ion exchanged with aqueous ruthenium chloride, dried, and reduced with hydrogen at 150°C. for 30 minutes. This catalyst is designated herein as Catalyst T.

Catalyst R, S, and T were tested according to the procedure of Example 1, except that the first stage conditions were 160° and 30 minutes in each case, and the second stage conditions were 175° and 90 minutes (60 minutes in the testing of catalyst R). Catalyst R was tested for only one cycle, but catalysts S and T were tested through four cycles each. Catalyst R gave a final pH of 5.5 and a total sugar analysis of 17.2% on the dry basis, and was not analyzed further. Catalyst S, although it gave acceptable final pH values (about 3.8), nevertheless gave total sugar values of about 5% in every cycle, and complete analysis was not made. Catalyst T, on the other hand, gave good results in every cycle except the first. Sorbitol assays (excluding the first cycle) ranged from 91.8% to 92.5%, and total sugar values ranged from 0.89% to 0.17%. The high sugar values with catalyst R and S show that hydrolysis of oligosaccharides was not complete, and that these catalysts are not suitable. The results obtained with catalyst T are comparable to those obtained with other low sodium catalysts in Examples 1 and 2. The good yield of sorbitol after treatment of the catalyst support to remove sodium shows that low sodium content is beneficial in catalysts used to treat polysaccharides.

EXAMPLE 12

This example shows that good conversion of glucose to sorbitol is obtained with a ruthenium on zeolite Y catalyst, even though the zeolite has a high sodium content.

The catalyst used in this example was 1% Ru on zeolite Y, (Na form).

A solution of glucose in water was prepared by dissolving 100 grams of glucose in approximately 100 ml. of water. 3 g. of catalyst was added and the slurry was charged to a one-liter autoclave. The initial pH of the catalyst/sugar slurry was 6.2.

The autoclave was pressured with hydrogen, heated to 160°C. and 1960 psig., and held at 160°C. for 35 minutes. The pressure dropped to 1760 psig. during this tme. The autoclave contents were cooled to room temperature, discharged from the autoclave, and filtered to separate the catalyst. The final pH of the reaction product was 5.5.

Analysis of the reaction product showed, on the dry basis, 93.8% sorbitol, 3.18% hexitans, 0.04% reducing sugar, and 0.53% total sugar.

Comparison of Examples 11 and 12 shows that the presence of appreciable quantities (more than about 1%) of Na is detrimental when the starting material is corn starch hydrolyzate but not detrimental when the starting material is glucose.

What is claimed is:

1. A process for the production of a polyhydric alcohol from a carbohydrate selected from the group consisting of monosaccharides, readily hydrolyzable polysaccharides and mixtures thereof, which comprises contacting said carbohydrate in an aqueous medium with hydrogen at a temperature in the range of about 100° to about 200°C and a pressure of at least about 100 psig. in the presence of a ruthenium-containing aluminosilicate zeolite catalyst of the molecular sieve type having pores of uniform size and having a silica/alumina mol ratio of at least about 3.

2. A process according to claim 1 in which said alumina/silicate zeolite is a zeolite of the Y type.

3. A process according to claim 1 in which said catalyst contains about 0.1% to about 5% by weight of ruthenium.

4. A process according to claim 3 in which said ruthenium is present as the free metal.

5. A process according to claim 1 in which the weight ratio of ruthenium to carbohydrate is in the range of about 0.01% to about 0.1%.

6. A process according to claim 1 in which the pH of said aqueous medium is at least about 3.

7. A process according to claim 1 in which said carbohydrate is a polysaccharide-containing carbohydrate.

8. A process according to claim 7 in which said carbohydrate is a starch or cellulose hydrolyzate.

9. A process according to claim 8 in which said carbohydrate is a starch hydrolyzate.

10. A process according to claim 9 in which said starch hydrolyzate is corn starch hydrolyzate.

11. A process according to claim 7 in which the reaction between said carbohydrate and hydrogen is carried out in two stages, the first stage being carried out at a temperature in the range of about 100 to about 175°C. and the second stage being carried out at a temperature of about 170 to about 200°C.

12. A process according to claim 7 in which the pH of the reaction medium is in the range of about 3.0 to about 4.5.

13. A process according to claim 1 in which said zeolite has an effective pore size in the hydrogen form of at least about 8 Angstrom units.

* * * * *